（12) United States Patent
Mount

(10) Patent No.: US 8,431,403 B2
(45) Date of Patent: Apr. 30, 2013

(54) METHOD FOR DETECTING ANALYTES

(75) Inventor: Andy Mount, Edinburgh (GB)

(73) Assignee: ITI Scotland Limited, Glasgow (GB)

( * ) Notice: Subject to any disclaimer, the term of this patent is extended or adjusted under 35 U.S.C. 154(b) by 408 days.

(21) Appl. No.: 12/522,751

(22) PCT Filed: Jan. 14, 2008

(86) PCT No.: PCT/EP2008/050351
§ 371 (c)(1),
(2), (4) Date: Jul. 10, 2009

(87) PCT Pub. No.: WO2008/084114
PCT Pub. Date: Jul. 17, 2008

(65) Prior Publication Data
US 2010/0065429 A1 Mar. 18, 2010

(30) Foreign Application Priority Data

Jan. 12, 2007 (GB) .................................. 0700640.6

(51) Int. Cl.
*G01N 15/06* (2006.01)
*G01N 33/00* (2006.01)
*G01N 33/48* (2006.01)

(52) U.S. Cl.
USPC ............. 436/43; 436/149; 436/164; 436/171; 436/172; 422/68.1; 422/82.01; 422/82.05; 422/82.07; 422/82.08; 422/82.09

(58) Field of Classification Search .................... 436/43, 436/149, 164, 171, 172; 422/68.1, 82.01, 422/82.05, 82.07, 82.08, 82.09
See application file for complete search history.

(56) References Cited

U.S. PATENT DOCUMENTS 5,344,535 A  9/1994 Betts et al.
(Continued)

FOREIGN PATENT DOCUMENTS

GB  2361883 A  7/2001
JP  2004132848  4/2004
JP  2005283560  10/2005

OTHER PUBLICATIONS

Consalvo, Daniela, International Search Report and Written Opinion, Date of Completion of International Search: Apr. 16, 2008, International Application No. PCT/EP2008/050351.

(Continued)

*Primary Examiner* — Brian J Sines
(74) *Attorney, Agent, or Firm* — Gavrilovich, Dodd & Lindsey, LLP; Joseph R. Baker, Jr.

(57) ABSTRACT

Provided is method for detecting an analyte, wherein the analyte is labelled with one or more labels relatable to the analyte which are suitable for optical detection, which method comprises: a) applying an oscillating voltage having a first frequency across the labelled analyte and simultaneously performing an optical detection method on the labelled analyte to obtain data from the one or more labels; b) applying an oscillating voltage having a second frequency across the labelled analyte and simultaneously performing an optical detection method on the labelled analyte to obtain data from the one or more labels; c) determining the identity and/or quantity of the analyte from the data obtained in step (a) and step (b).

14 Claims, 2 Drawing Sheets

U.S. PATENT DOCUMENTS

| | | |
|---|---|---|
| 6,403,367 B1 | 6/2002 | Cheng et al. |
| 2005/0069932 A1* | 3/2005 | Arinaga et al. .................... 435/6 |
| 2006/0003437 A1* | 1/2006 | Fujihara et al. ............ 435/287.1 |
| 2006/0040378 A1* | 2/2006 | Arinaga et al. ............ 435/287.2 |
| 2006/0148102 A1 | 7/2006 | Guo et al. |
| 2007/0048760 A1* | 3/2007 | Arinaga et al. .................... 435/6 |
| 2008/0003666 A1* | 1/2008 | Arinaga et al. ............ 435/287.2 |

OTHER PUBLICATIONS

Williams, Claire, Patents Act 1977: Search Report under Section 17, Date of Search: May 17, 2007, Application No. GB0700640.6.

Ito, Hiromi, Notice of Reasons for Rejection, JP 2009-545196, Japanese Patent Office, Aug. 2, 2011.

* cited by examiner

METHOD FOR DETECTING ANALYTES

CROSS REFERENCE TO RELATED APPLICATIONS

The present application is a National Stage Application filed under 35 USC §371 and claims priority to International Application No. PCT/EP08/050,351, filed Jan. 14, 2008, which application claims priority to Great Britain Application No. 0700640.6, filed Jan. 12, 2007, the disclosures of which are incorporated herein by reference.

The present invention relates to a method for detecting an analyte using simultaneous optical and electrochemical processes to obtain data on the analyte. The method is advantageous since it may result in enhanced sensitivity over optical or electrochemical methods alone.

The modulation of light emission during electrochemical impedance spectroscopy is known, and has been used in research to characterise electro-chemiluminescent systems, e.g. in the following publications:

Itagaki, Masayuki; Kasugai, Emi; Kobari, Nao; Watanabe, Kunihiro. "Electrochemiluminescence of luminol investigated by electrochemical impedance spectroscopy." Electrochemistry (Tokyo, Japan) (2001), 69(2), 104-108. CODEN: EECTFA ISSN:1344-3542. CAN 134:154451 AN 2001:108323 CAPLUS.

Itagaki, Masayuki; Kobari, Nao; Watanabe, Kunihiro "Electrochemiluminescence impedance of perylene in acetonitrile." Journal of Electroanalytical Chemistry (2004), 572 (2), 329-333. CODEN: JECHES CAN 141:428860 AN 2004: 809295 CAPLUS.

Itagaki, Masayuki; Kikuchi, Takahiro; Watanabe, Kunihiro. "Electrochemiluminescence of N-(4-aminobutyl)-N-ethylisoluminol investigated by electrochemical impedance spectroscopy." Analytical Sciences (1999), 15(8), 755-760. CODEN: ANSCEN ISSN:0910-6340. CAN 131:206351 AN 1999:515415 CAPLUS.

Modulated light intensity to generate and analyse modulated photocurrents and modulated electric fields to generate modulated light output have been used in the analysis of semiconductors and solar cells e.g. in the following:

"Phase-shift analysis of modulated photocurrent: Its application to the determination of the energetic distribution of gap states." Oheda, Hidetoshi. Electrotech. Lab., Ibaraki, Japan. Journal of Applied Physics (1981), 52(11), 6693-700. CODEN: JAPIAU ISSN: 0021-8979. Journal written in English. CAN 95:230432 AN 1981:630432 CAPLUS.

Garuthara, Rohana; Tomkiewicz, Micha; Silberstein, Robert P. "Electric field modulation of photoluminescence in cadmium selenide liquid junction solar cells." Journal of Applied Physics (1983), 54(11), 6787-9. CODEN: JAPIAU ISSN:0021-8979. CAN 99:215717 AN 1983:615717 CAPLUS Modulated impedance photocurrents have also recently been used in polymer imaging:

Krause, Steffi; Moritz, Werner; Talabani, Habib; Xu, Ming; Sabot, Andrea; Ensell, Graham. "Scanning Photo-Induced Impedance Microscopy-Resolution studies and polymer characterization." Electrochimica Acta (2006), 51(8-9), 1423-1430. CODEN: ELCAAV ISSN:0013-4686. AN 2006: 56265 CAPLUS Current electrochemical impedance analysis typically involves measuring the impedance response from the current-voltage response over a wide frequency range. This electrochemical response is dominated by particular physical processes (e.g. diffusion, adsorption, electrochemical reaction) at their characteristic frequencies. Impedance analysis enables these processes to be identified.

Some research has been carried out on using impedance spectroscopy for label-free detection of bio-molecules, e.g. E. Katz & I. Willner, "Probing biomolecular interactions at conductive and semiconductive surfaces by impedance spectroscopy: Routes to impedimetric immunosensors, DNA-sensors, and enzyme biosensors", Electroanalysis 2003, 15, 913.

However, the above techniques when adapted to the detection of bio-molecules are still in need of improvement. It is an aim of the present invention to solve the problems associated with known methods, and to develop a detection method with improved sensitivity and/or selectivity, in particular for biomolecular analytes.

Accordingly, the present invention provides a method for detecting an analyte, wherein the analyte is labelled with one or more labels relatable to the analyte which are suitable for optical detection, which method comprises:

(a) applying an oscillating voltage having a first frequency across the labelled analyte and simultaneously performing an optical detection method on the labelled analyte to obtain data from the one or more labels;
(b) applying an oscillating voltage having a second frequency across the labelled analyte and simultaneously performing an optical detection method on the labelled analyte to obtain data from the one or more labels;
(c) determining the identity and/or quantity of the analyte from the data obtained in step (a) and step (b).

In the context of the present invention, the term "oscillating" encompasses all potential waveform shapes, including (but not limited to) sinusoidal waves, saw tooth waves, square waves and pulses.

As mentioned above, the present invention is made on the basis that the combination of electrochemical and optical readout may confer advantages in the detection of analytes, such as bio-molecules and other species, over either technique on its own, either by improving sensitivity or specificity, or both. For combined fluorescence (or luminescence) and electrochemical detection systems, it may be advantageous to simultaneously measure the frequency of light emission during electrochemical perturbation and determine the in-phase and out-of-phase components of this emission. This may enable the effect of coupling of the electrochemical perturbation and fluorescence output to be measured as a function of frequency, which may determine the optimum frequencies for enhanced sensitivity (as analysing only the coupled signal should reduce background) and specificity (as there may be an optimum driving frequency for a particular target molecule) in a particular combined system.

In the present invention, typically the frequency of the oscillating voltage is moved through a frequency range (from the first frequency to the second frequency), and optical detection is performed simultaneously with the changing voltage to obtain data from the one or more labels over the frequency range. In some embodiments of the invention, a DC voltage may also be applied to the system at the same time as the oscillating voltage. This may be used to control the oxidation state and/or field experienced by the analyte (e.g. a bio-molecule) and thereby optimise the response.

The oscillating voltage is not especially limited, provided that it delivers useful data in combination with the optical measurement. However, it is preferred that the amplitude of the oscillating voltage at the analyte is between 100 µV and 2.5 V. The upper limit of the voltage range is set by the solvent limit for water or equivalent solvent in which the analysis is being carried out, whereas the lower limit is set by the signal to noise response of the electrochemical detection circuitry. It must be remembered that overall applied voltages of much greater than this may be possible and/or desirable if the voltage is applied across a resistive surface film, whereby the majority of the voltage is applied across this film, resulting in a voltage within the preferred range being applied at the analyte. It is preferred that the voltage at the analyte is more usefully in the range 1 mV to 1 V. The upper limit may help to ensure that no unwanted electrochemical redox reaction occurs. It is further preferred that this voltage may usefully be in the range 5 mV to 0.1 V, and particularly towards the lower end of this amplitude scale, where linearisation of the electrochemical response simplifies theoretical analysis (although this may not be crucial).

The frequency of the oscillating voltage is not especially limited, provided that it does not adversely affect the method. However, in preferred embodiments of the invention the range of the first frequency to the second frequency is from 1 mHz to 1 MHz. At these frequencies, inductive effects, electrolyte ion motion, polarisation, double layer charging, analyte structural and conformational change, charged analyte motion, counter-ion and redox ion motion and changes in solvation can all occur, which can give rise to changes in the optical signal output through changes in the local environment of the optical label. In further preferred embodiments, the frequency range of the first frequency to the second frequency is from 1 mHz to 100 kHz and more preferably from 1 mHz to 10 kHz. At the high frequency end of this range, electrode double layer charging typically occurs; at intermediate frequencies, electrode redox reaction, diffusion of ions and solvent and relatively small analyte motion occurs; at the lower frequency range, the motion of large species such as polymers and large analyte species occurs.

In some aspects the present method may operate without labelling the analyte, provided that the analyte contains some moiety that may act as a label (and in the context of the present invention, such moieties are considered to be labels i.e. they are intrinsic labels) to allow optical analysis (and if desired also electrochemical analysis) of the analyte. The intrinsic label(s) may thus be optical label(s) and, where electrochemical measurement is to be taken in addition to optical measurement, electrochemical label(s). However, in preferred embodiments, before step (a), the method further comprises the step of labelling the analyte with the one or more labels to form the labelled analyte.

The present invention also provides a method for detecting a plurality of analytes, wherein the each different analyte is labelled with one or more different labels relatable to the analyte, which are suitable for optical detection, which method comprises:

a) applying an oscillating voltage having a first frequency across the labelled analytes and simultaneously performing an optical detection method on the labelled analytes to obtain data from the one or more labels;

b) applying an oscillating voltage having a second frequency across the labelled analytes and simultaneously performing an optical detection method on the labelled analytes to obtain data from the one or more labels;

c) determining the identity and/or quantity of the plurality of analytes from the data obtained in step (a) and step (b).

In this method it is also preferred that before step (a), the method further comprises the step of labelling the plurality of analytes with the one or more labels to form the plurality of labelled analytes.

The labels are not especially limited. However, in preferred embodiments the labels are selected from fluorescent labels; these include fluorescein and its derivatives, rhodamine and its derivatives, lanthanide complexes, cyanine dyes (Cy3, Cy5, Atto labels) and Quantum Dots, each of which can be covalently attached to biomolecular systems.

In all of the methods of the present invention, it is typical that the data contain information on the effect of the frequency of the oscillating voltage on the optical emission intensity, changes in the emission lifetime and/or the frequency of light emitted or absorbed by the one or more analytes (intrinsic labels), and/or labels attached to the analytes (extrinsic labels). Changes in emission and absorption frequency can result from variation in the chemical or environmental nature of the analyte or label, for example brought about by alterations in the degree of protonation (e.g. from changes in pH) or brought about by alterations in the degree of complexation (e.g. from changes in complexant proximity and/or concentration) or local environment (e.g. solvation). Changes in emission lifetime can be observed as a consequence of variation in the environment surrounding the analyte or label (e.g. changes in solvation, local dielectric constant through changes in local composition, and alteration in energy transfer to neighbouring species due to changes in separation). Such changes also lead to a change in the observed emission intensity (as the observed emission intensity is governed by the emission lifetime and the number of emitting species). Thus, the present invention extends to any changes in optical characteristics brought about by electrochemical perturbation, whether simple changes in the environment of the fluorophore brought about by non-Faradaic processes such as ion movement and changes in solvation, as discussed above, or by more complex effects.

Typically the optical detection method is selected from optical emission detection, optical absorbance detection, optical scattering detection, spectral shift detection, surface plasmon resonance imaging, and surface-enhanced Raman scattering or dual polarisation interferometry from adsorbed dyes.

Typically, the optical detection method is optical emission detection. This may include, for example, fluorescence methods comprising the steps of irradiating the labelled analytes with light capable of exciting the labels and detecting the frequency and intensity of light emissions from the labels. Typically the light is laser light. The frequency of the light is typically selected from infra-red light, near infra-red light, visible light, and UV light. However, fluorescence is not the only method, and (for example) electrochemiluminescent methods may also be employed.

The present method is preferably directed to analytes that are bio-molecules, although any analytes may be assayed, if desired. In preferred embodiments, the analyte comprises one or more compounds selected from a cell, a protein, a polypeptide, a peptide, a peptide fragment, an amino acid, a carbohydrate, a lipid, a synthetic chemical, and DNA or RNA including oligonucleotides polynucleotides and nucleotides thereof.

The present invention will now be described in further detail, by way of example only, with reference to the following Figures, in which.

Figure 1:
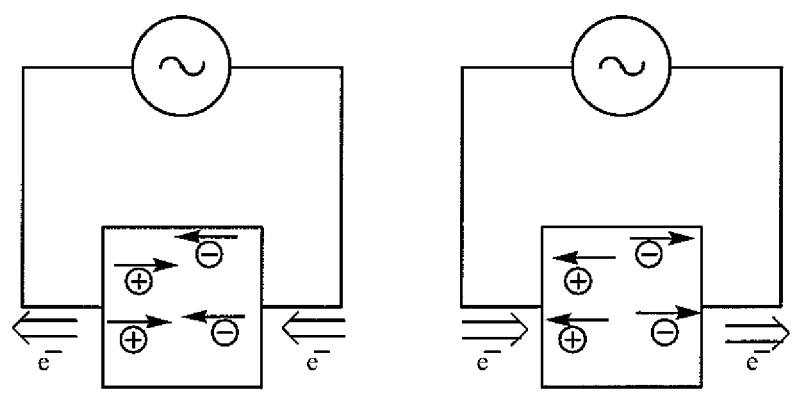
FIG. 1 shows the effect of an oscillating sinusoidal voltage applied across a solution containing charged species.

The present invention will now be described in more detail. In this invention, electrochemical perturbation and optical measurement are made simultaneously. The principle behind the technology is as follows. An oscillating sinusoidal voltage is applied across a solution containing charged species (see FIG. 1), causing a current to flow. If desired, the current passing through the solution may also be measured. The species will behave differently depending upon the frequency of the oscillation. This behaviour will also depend upon the composition of the solution and the surrounding conditions (temperature, pressure, local environment of the species). This is because these factors will affect the mobility of the species in the solution. High frequency and/or low mobility give rise to simple oscillation of the species (as illustrated in the Figure) which in fact looks like simple resistance (conductance). Low frequency and/or high mobility allows the species to be displaced from their original mean position, leading to charge polarisation and associated solvent transfer, typically leading to a Warburg resistance. At the limit of low frequency, bulk polarisation can occur, which leads to the formation of charged double layers at the electrodes; this looks like a simple capacitance. In addition, redox-active species can reach the electrodes and undergo redox reaction at the surface, leading to a charge transfer resistance.

Known electrochemical methods involve varying the applied frequency, and measuring the changes in current. Because these changes depend on the identity (charge, mobility and redox activity) of the species in the solution, they provide information on the species and processes occurring in the local environment of the species. Clearly, a binding event, or an event which perturbs the environment near the species, greatly affects mobility for all species, and charge transfer for redox active species. The methods may be usefully employed to detect binding in biological molecules. Typically the frequency is progressively lowered and the characteristic resistances (conductances) and capacitances measured.

As has been said, in the present invention, the electrochemical methods are combined with an optical measurement. In a system such as the one above, the frequency of light emission from a label is typically constant, but the intensity may change with the frequency of the applied electrochemical perturbation. This is because the electrochemical method leads to a perturbation of the local environment around the species. If this is in close proximity to the label (or the species is itself also the label, i.e. the label is intrinsic), changes in the local label environment will occur, which affect the emission lifetime and hence the emission intensity. At lower frequencies, changes in environment can occur over greater distances from the original location of the species, which can affect more labels or labels located further away from each species. The intensity and/or frequency of the emitted light can be measured, and the effect of the frequency of oscillation of the voltage on the intensity and/or frequency of the emitted light can also be measured. As has been said, typically it is expected that it will be the emission lifetime (and hence intensity) of the emitted light that changes with the frequency of the applied voltage, and it is this change in intensity that is measured. However, it may be the frequency of the emitted light that changes, or both frequency and intensity, depending on the nature of the system and species under investigation. The relationship generally depends on the nature of the species, and the effect of the perturbation that they induce on the local environment of the label. Phase sensitive detection of the light may also be employed, i.e. the modulation in the light intensity is measured as a function of the frequency of the applied voltage.

To re-iterate, in a typical system of the present invention, a particular analyte or species (typically redox inactive in the chosen voltage range) is investigated by applying an oscillating voltage and measuring the intensity and/or frequency of emitted light from the species. In some embodiments the electric current passing through the species may also be measured, but this is not essential.

It will be apparent to the skilled person that the present invention can be adapted in a variety of ways, depending on the species under investigation. In the following some significant aspects and specific embodiments are envisaged.

Aspect 1—the Fluorescing Species is Excited by Electrochemiluminescence

Energy needs to be transferred into the fluorescent species in order for light to be emitted. For electrochemiluminescence, this energy is provided by electrochemical generation of one or more redox species which take part in a spontaneous redox or chemical reaction, often with an optical label, to provide this energy.

It is thus necessary for the redox energy to be transferred into the fluorescent moiety (the optical label) in sufficient quantity for fluorescence to occur. If the fluorescing moiety is too far from the site of generation of the redox species, then dissipation of the energy may preclude fluorescence.

Figure 2:
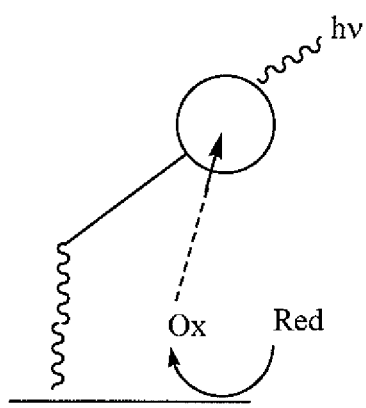
FIG. 2 shows a chemiluminescent system where energy is transferred by a third species to a luminescent moiety in an analyte.

For example, a 3rd party species in a reduced state (e.g. Red) is first excited at an electrode to produce an oxidised species (e.g. Ox, such as hydrogen peroxide), which then diffuses to the fluorescing moiety (e.g. luminol), as depicted in FIG. 2. The efficiency of electrochemiluminescence (the intensity of fluorescent light) will therefore correlate with the amount of redox species generated at the electrode and the distance over which this species is able to diffuse to induce electrochemiluminescence at the fluorescent moiety. This can be controlled by the frequency and amplitude of the voltage applied to the electrode; the amplitude and DC potential of the voltage can be set to control how much of the $3^{rd}$ party species is generated (and removed) at the electrode, and the frequency controls how far the generated $3^{rd}$ part species can diffuse away from the electrode. This, the intensity can be controlled by changing the characteristics of the applied voltage.

Aspect 2—the Fluorescing Species is Excited by Light and Affected by Electrochemistry (for Example, it has 2 or More Redox States)

This example operates in exactly the same way as the typical system discussed above, except is potentially more interesting from an informational viewpoint. The light intensity and/or frequency in a first oxidation state responds differently to the oscillating voltage than the corresponding intensity and/or frequency in second and/or further redox states. Therefore, more information is forthcoming than for a single redox state.

Aspect 3—Nucleotide Hybridisation Assays

A further embodiment that may be employed in the typical system, or in Aspects 1 and 2 is a system which is specific to hybridisation reactions, e.g. using an intercalating dye.

As has been referred to in Aspect 2, some fluorescent labels which can be used as tags in bio-systems are also redox active, being able to switch between fluorescent and less or non-fluorescent states. Those that do not, can also have their fluorescence output reduced or eliminated by quenching species. Modulation of the voltage on an underlying electrode surface onto (or adjacent electrode surface near) which labelled species (such as oligonucleotides) have been immobilised by standard immobilisation procedures will produce a modulation in fluorescence output from the label (either through direct redox reaction or via reaction with a soluble redox mediator or quencher). This change in light output is typically measured through use of a suitable detector e.g. a photovoltaic, which can measure the light intensity of the emitted light. One can also measure the phase sensitive response of the light output to the applied voltage perturbation. One useful method of analysis includes measuring both the light response and current response by analysing the ratio of photovoltaic voltage to applied voltage (this may be termed fluorescence impedance) as a function of frequency (fluorescence impedance spectroscopy) and the ratio of current to applied voltage as a function of frequency (termed impedance spectroscopy). The extent of light and current output modulation (both in-phase and out-of-phase) as a function of the frequency of the applied voltage will be determined by such factors as the rate of diffusion and/or migration of the mediator or quencher through the immobilised oligonucleotides, the rate of reaction (which may be affected by the availability of the label for reaction) and the distance of the label from the electrode surface. Any or all of these factors may change significantly upon specific oligonucleotide hybridisation, as indeed they may with non-specific binding. However, the combination of all of these measurements (light modulation, current modulation and frequency) may lead to a characteristic and distinct change in the measured light impedance and impedance spectral data either alone or in combination indicative of specific binding and distinct from non-specific binding.

EXAMPLE 1

Modulation of Fluorescence Output of Fluorescein with Applied AC Voltage

A pair of gold interdigitated electrodes, each having five fingers and with width and finger separation 5 μm is prepared so as to enable the application of an alternating voltage between the electrodes into a thin gel film of agarose.

Different fluorescein isothiocyanate (FITC) fluorophore concentrations, are prepared from a stock solution in ethanol (50 μg/ml, 10 μg/ml, and 1 μg/ml) in 1% Agarose gel (1% Agarose in TEA buffer—40 mM Tris™ buffer, 2 mM NaEDTA, 20 mM Na-acetate, pH 7.8). The thickness of the thin film of FITC/agarose, (made liquid by heating in a microwave), is controlled by deposition using Scotch tape or a GeneFrame™ to define a perimeter of thickness 4 μm, 8 μm or 500 μm as appropriate.

Cooling to room temperature results in gel formation. This is covered with a glass cover slip. Fluorescence spectra are measured with a FluoroMax-3 (Horiba Jobin Yvon) fluorescence spectrometer, exciting at 495 nm, the peak excitation wavelength, and measuring the emission spectrum between 505 and 550 nm.

Fluorescence is collected away from the specular angle, to optimise signal-to-noise. The AC voltage is applied with an Autolab PGSTAT 12 potentiostat between the interdigitated electrodes, with a Frequency Response Analyser (FRA) module, using a DC voltage of 0 V and AC frequencies of 10 kHz, 1 kHz, 100 Hz, 10 Hz, and 1 Hz, and RMS amplitudes of 10 mV, 100 mV, and 350 mV.

The magnitude of the variation in fluorescence intensity will depend on the applied frequency and amplitude of the applied AC voltage. From this, information on the fluorescein environment may be inferred.

The invention claimed is:

1. A method for detecting an analyte, wherein the analyte is labelled with one or more labels relatable to the analyte which are suitable for optical detection, which method comprises:
    (a) applying an oscillating voltage having a first frequency across the labelled analyte and simultaneously performing an optical detection method on the labelled analyte to obtain data from the one or more labels;
    (b) applying an oscillating voltage having a second frequency across the labelled analyte and simultaneously performing an optical detection method on the labelled analyte to obtain data from the one or more labels;
    (c) measuring the frequency of light emission during electrochemical perturbation in steps (a) and (b) and determining the identity and/or quantity of the analyte from the data obtained, wherein the frequency of the oscillating voltage is moved through a range of frequencies from the first frequency to the second frequency and optical detection is performed simultaneously with the changing voltage to obtain data from the one or more labels over the range of frequencies.

2. A method according to claim 1 for detecting a plurality of analytes, wherein each different analyte is labelled with one or more different labels relatable to the analyte.

3. A method according to claim 1, wherein the oscillating voltage is a voltage of from 100 μV to 2.5 V.

4. A method according to claim 1, wherein the first frequency is 1 mHz or more and the second frequency is 1 MHz or less.

5. A method according to claim 1, wherein before step (a), the method further comprises the step of labelling the analyte with the one or more labels to form the labelled analyte.

6. A method according to claim 1, wherein the data comprises information on the effect of the frequency of the oscillating voltage on the intensity and/or the frequency of light emitted or absorbed by the one or more labels.

7. A method according to claim 1, wherein the labels are fluorescent labels.

8. A method according to claim 7, wherein the fluorescent labels are selected from fluorescein and its derivatives, rhodamine and its derivatives, lanthanide complexes, cyanine dyes including Cy3 Cy5 and Atto Labels, and Quantum Dots.

9. A method according to claim 1, wherein the optical detection method is selected from optical emission detection, optical absorbance detection, optical scattering detection, spectral shift detection, surface plasmon resonance imaging, and surface-enhanced Raman scattering from adsorbed dyes.

10. A method according to claim 9, wherein the optical detection method is optical emission detection and comprises the steps of irradiating the labelled analytes with light capable of exciting the labels and detecting the frequency and/or intensity of light emissions from the labels.

11. A method according to claim 10, wherein the light is laser light.

12. A method according to claim 10 or claim 11, wherein the light is selected from infra-red light, visible light and UV light.

13. A method according to claim 1, wherein the analyte comprises one or more compounds selected from a cell, a protein, a polypeptide, a peptide, a peptide fragment, an amino acid, DNA or RNA and oligonucleotides polynucleotides or nucleotides thereof.

14. A method according to claim 1, wherein one or more of the labels relatable to the analyte are intrinsic labels.

* * * * *